United States Patent
Gindre et al.

(10) Patent No.: US 12,248,887 B2
(45) Date of Patent: *Mar. 11, 2025

(54) METHOD AND APPARATUS FOR PREDICTING A RACE TIME

(71) Applicant: Slyde Analytics LLC, Houston, TX (US)

(72) Inventors: Cyrille Gindre, Leysin (CH); Frederic Lamon, Corin-de-la-Crête (CH); Christophe Ramstein, Haut-Nendaz (CH); Patrick Flaction, Chandolin-Pres-Saviese (CH)

(73) Assignee: Slyde Analytics LLC, Houston, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 18/199,823

(22) Filed: May 19, 2023

(65) Prior Publication Data

US 2023/0368053 A1   Nov. 16, 2023

Related U.S. Application Data

(63) Continuation of application No. 16/339,256, filed as application No. PCT/IB2017/056159 on Oct. 5, 2017, now Pat. No. 11,687,809.

(30) Foreign Application Priority Data

Oct. 6, 2016   (CH) ................. CH01331/16

(51) Int. Cl.
*G06N 5/00* (2023.01)
*A61B 5/00* (2006.01)
(Continued)

(52) U.S. Cl.
CPC ............ *G06N 5/048* (2013.01); *A61B 5/1112* (2013.01); *A61B 5/1118* (2013.01); *A61B 5/112* (2013.01);
(Continued)

(58) Field of Classification Search
CPC ... A63K 3/00; G07C 1/22; G07C 1/24; G06N 5/048; G06N 7/005; G06N 7/02; G06N 7/023; G06N 7/026
(Continued)

(56) References Cited

U.S. PATENT DOCUMENTS

| 6,837,827 B1 | 1/2005 | Lee |
| 7,572,205 B1 | 8/2009 | Cribar |

(Continued)

FOREIGN PATENT DOCUMENTS

| WO | WO-02/39363 A1 | 5/2002 |
| WO | WO-2015/144851 A1 | 10/2015 |

OTHER PUBLICATIONS

International Search Report and Written Opinion for PCT/IB2017/056159 dated Jan. 18, 2018, 13 pages.
(Continued)

*Primary Examiner* — Hai L Nguyen
(74) *Attorney, Agent, or Firm* — Volpe Koenig (57) ABSTRACT

A method and system for optimizing an athlete's performance during a race using a wearable device. The method involves determining the athlete's performance level from past races or trainings, and collecting race data through a wearable sensor. This data helps retrieve a tailored race profile from several options, each a non-linear function of time over distance, optimized for the athlete's level. The selected profile is applied to the sensor data to compute a projected race time, which is then displayed on the device. The system also measures and displays other race param-
(Continued)

eters such as stride length, cadence, and physiological metrics. It adjusts recommendations for pace in real-time based on these inputs. Advanced features include neural networks for enhancing race profile accuracy using data from multiple athletes. The device's processor and memory manage these functions effectively, providing dynamic feedback and strategic adjustments during the race, aiming to significantly improve athletic performance.

22 Claims, 11 Drawing Sheets

(51) Int. Cl.
| | |
|---|---|
| *A61B 5/11* | (2006.01) |
| *A63K 3/00* | (2006.01) |
| *G06N 5/048* | (2023.01) |
| *G06Q 10/04* | (2023.01) |
| *G07C 1/24* | (2006.01) |
| *G09B 19/00* | (2006.01) |
| *G16H 20/30* | (2018.01) |
| *G16H 50/30* | (2018.01) |

(52) U.S. Cl.
CPC ............ *A61B 5/1122* (2013.01); *A61B 5/681* (2013.01); *A61B 5/7264* (2013.01); *A61B 5/7275* (2013.01); *A63K 3/00* (2013.01); *G06Q 10/04* (2013.01); *G07C 1/24* (2013.01); *G09B 19/0038* (2013.01); *G16H 20/30* (2018.01); *G16H 50/30* (2018.01); *A61B 5/6803* (2013.01); *A61B 5/6807* (2013.01); *A61B 2503/10* (2013.01); *A61B 2562/0219* (2013.01)

(58) Field of Classification Search
USPC ......................................................... 482/3, 8
See application file for complete search history.

(56) References Cited

U.S. PATENT DOCUMENTS

| | | | |
|---|---|---|---|
| 7,946,960 B2 | 5/2011 | Vitolo | |
| 11,687,809 B2 * | 6/2023 | Gindre | ............... G09B 19/0038 482/3 |

OTHER PUBLICATIONS

Garmin, "Garmin Forerunner 230/235 Owner's Manual"; http://static.garmin.com/pumac/Forerunner_230_OM_EN.pdf; Dec. 31, 2015, pp. 1-20.

* cited by examiner

| VO2MAX | 3 km | 5 km | 10 km | 15 km | 20 km | 30 km | 42 km |
|---|---|---|---|---|---|---|---|
| 68 | 0:09:34 | 0:16:34 | 0:35:01 | 0:54:19 | 1:14:14 | 1:55:25 | 2:47:29 |
| 67 | 0:09:44 | 0:16:52 | 0:35:40 | 0:55:21 | 1:15:41 | 1:57:43 | 2:50:55 |
| 66 | 0:09:54 | 0:17:10 | 0:36:20 | 0:56:25 | 1:17:10 | 2:00:07 | 2:54:30 |
| 65 | 0:10:05 | 0:17:29 | 0:37:02 | 0:57:32 | 1:18:43 | 2:02:35 | 2:58:12 |
| 64 | 0:10:15 | 0:17:48 | 0:37:44 | 0:58:41 | 1:20:19 | 2:05:10 | 3:02:02 |
| 63 | 0:10:26 | 0:18:08 | 0:38:29 | 0:59:52 | 1:21:58 | 2:07:50 | 3:06:01 |
| 62 | 0:10:38 | 0:18:29 | 0:39:15 | 1:01:05 | 1:23:41 | 2:10:36 | 3:10:10 |
| 61 | 0:10:50 | 0:18:50 | 0:40:02 | 1:02:21 | 1:25:28 | 2:13:28 | 3:14:29 |
| 60 | 0:11:02 | 0:19:12 | 0:40:51 | 1:03:40 | 1:27:18 | 2:16:27 | 3:18:58 |
| 59 | 0:11:15 | 0:19:35 | 0:41:42 | 1:05:02 | 1:29:13 | 2:19:33 | 3:23:38 |
| 58 | 0:11:28 | 0:19:58 | 0:42:35 | 1:06:27 | 1:31:13 | 2:22:47 | 3:28:30 |
| 57 | 0:11:41 | 0:20:22 | 0:43:30 | 1:07:55 | 1:33:17 | 2:26:09 | 3:33:35 |
| 56 | 0:11:55 | 0:20:48 | 0:44:26 | 1:09:27 | 1:35:26 | 2:29:40 | 3:38:53 |
| 55 | 0:12:10 | 0:21:14 | 0:45:25 | 1:11:02 | 1:37:41 | 2:33:19 | 3:44:25 |
| 54 | 0:12:24 | 0:21:41 | 0:46:27 | 1:12:42 | 1:40:01 | 2:37:08 | 3:50:13 |
| 53 | 0:12:40 | 0:22:09 | 0:47:31 | 1:14:25 | 1:42:28 | 2:41:08 | 3:56:17 |
| 52 | 0:12:56 | 0:22:38 | 0:48:36 | 1:16:13 | 1:45:00 | 2:45:18 | 4:02:39 |
| 51 | 0:13:13 | 0:23:09 | 0:49:46 | 1:18:05 | 1:47:40 | 2:49:40 | 4:09:19 |
| 50 | 0:13:30 | 0:23:40 | 0:50:58 | 1:20:03 | 1:50:27 | 2:54:15 | 4:16:20 |
| 49 | 0:13:48 | 0:24:13 | 0:52:13 | 1:22:06 | 1:53:22 | 2:59:04 | 4:23:42 |
| 48 | 0:14:06 | 0:24:47 | 0:53:32 | 1:24:14 | 1:56:25 | 3:04:06 | 4:31:27 |
| 47 | 0:14:26 | 0:25:22 | 0:54:53 | 1:26:29 | 1:59:37 | 3:09:25 | 4:39:38 |

MY RUNS

| | |
|---|---|
| Type | Training [Event] |
| Name | NY Marathon |
| Starts | 6 nov. 2016 à10:00:42 |
| Ends | 6 nov. 2016 à13:30:42 |
| Location | New York |
| Distance | 5k \| 10k \| 1/2 Marathon \| [Marathon] |
| Objective | 03:30 |
| Success probability | 100% |

START

Fig. 11

METHOD AND APPARATUS FOR PREDICTING A RACE TIME

RELATED APPLICATIONS

This application is continuation of U.S. patent application Ser. No. 16/339,256, filed on Apr. 3, 2019, now U.S. Pat. No. 11,687,809 B2 issued on Jun. 27, 2023, which is a national phase of PCT/IB2017/056159, filed on Oct. 5, 2017, which claims the benefit of Swiss Application No. 01331/16, filed on Oct. 6, 2016. The entire contents of these applications are hereby incorporated by reference in their entirety.

FIELD OF THE INVENTION

The present invention concerns a method and an apparatus for predicting a race time.

DESCRIPTION OF RELATED ART

In many sports such as running, cycling, swimming and other endurance sports, it would be desirable to determine the optimal pace in order to achieve a desired time target. For example, most marathoners predict a time performance, and adjust their pace during the race in order to achieve this target.

It is also known to measure the maximal oxygen consumption (VO2 max), for example on a motorized treadmill, and to determine the expected performance from this value. Tables have been computed in the prior art, such as the one shown on FIG. 1, that indicate the expected running performances over various distances for various values of VO2max. Many athletes therefore make a VO2max test in order to determine the optimal pace.

It is also known to predict a running or cycling time over a distance based on a time needed for a different distance. Multiplying factors have been determined from experiences with runners of different levels in order to determine those factors. For example, if a runner indicates his personal time to run 10 kilometres, his time for a marathon is likely to be about 5.1 time this value for a beginner, and 4.95 time this value for a good runner.

Those methods are useful in order to determine the ideal pace to run a race. In fact, the most energy-efficient way of running is to run the whole distance at a constant pace and thus avoiding energy expenses through accelerations and decelerations. However, it has been observed that most runners or cyclers tend to run at a non-ideal irregular pace; for example, many marathoners start too fast, either because they over-estimate themselves or because they are pulled by the crowd. As a consequence of this poor management of pace throughout the race, many are exhausted after 30 kilometres or so, and don't reach the predicted time target.

WO15144851 relates to a device including at least one accelerometer sensor, at least one data-processing unit producing instantaneous consumed-energy data depending on the acceleration data, and data predicting consumed energy, depending on the instantaneous energy data and chronometric data. The predictions of physiological parameters are based on the accelerations produced or applied by the person during a sport activity. This device informs an athlete in advance before he is exhausted.

WO0239363A1 is related to a computer-based method of conditioning and/or training a participant for a sporting event which includes storing in the computer desired performance data for a desired performance level in the sporting event; storing in the computer event data which is related to the sporting event; storing in the computer participant data which is related to a participant in the sporting event; developing from the stored data a conditioning and/or training schedule for the participant for the event, the schedule including a plurality of conditioning and/or training events; causing a participant to carry out the conditioning and/or training events; monitoring the participant's performance when carrying out the conditioning and/or training events, deriving training performance data relating thereto, and transmitting the training performance data to the computer; monitoring training event data relating to the conditioning and/or training events when being carried out by the participant and transmitting the training event data to the computer, and modifying the conditioning and/or training schedule and the plurality of conditioning and/or training events in response to the training performance data and training event data.

According to one aspect of the invention, it would be useful to verify at several instants during a race if the current pace is optimal or if the athlete should run or cycle slower or faster at each moment.

BRIEF SUMMARY OF THE INVENTION

According to an aspect of the invention, these aims are achieved with standard race profiles, and by determining which of those standard race profiles an athlete is currently following.

A race profile is a non-linear function of time over distance t=f(d). It could be for example an analytic function, or a histogram indicating the pace or time at various segments of a race.

It has been found that a vast majority of athletes follow one among a limited number of race profiles during a race. For example, many beginners at a marathon run faster during the first half of the marathon than during the second half. More experienced runners tend to run the whole distance at a more constant speed.

Therefore, standard race profiles could be determined by grouping athletes having a similar deviation from a constant pace over the whole race. Since the number of profiles is limited, it is possible to store them in a wearable device of the athlete and to make the prediction during the race, even if the wearable is not connected to a remote server.

It has been found that the standard profiles could be normalized and become independent from the time needed for a race. For example, marathoners who need 3 hours, 4 hours and 5 hours may be assigned to a common race profile if the deviations from a race at constant speed is proportionally the same at each intermediate time. For example, one race profile could be applied to all fast starters who start a race 5% faster than the average rate corresponding to their level or time target.

In one aspect, those means are also achieved with a method for updating and providing at least one of the following information to an athlete during a race such as a running or a cycling race:
  a race time prediction
  a probability to achieve a target time at the end of the race;
  and/or an indication whether the pace followed by the athlete is too fast, adequate or too slow in order to achieve a target time,
  said method comprising
  measuring during said race a plurality of intermediate times with an inertial sensor and/or a positional sensor in a wearable device;

causing a processing unit in said wearable device to retrieve a race profile as a non-linear function of time over distance (t=f(d));

using the retrieved race profile for determining said information.

The intermediate times are measured at predetermined distances determined with the inertial sensor or positional sensor, for example after each kilometre. The time itself at those distances might be measured with a clock or GPS system.

The race time prediction may for example indicate to a marathoner that he is likely to finish the marathon in 4 hours if he follows his current race profile. The prediction is updated at each new intermediate time, for example if the athlete deviates from the previously determined race profile.

The probability to achieve a target time at the end of the race may for example indicate to an athlete that his probability to achieve a marathon in less than 4 hours is less than 50% after 10 kilometres. Typically, this probability will decrease if the runner runs too slowly but also if he is running too fast. Therefore, the method may have the surprising effect of predicting a longer race time or a lower probability to achieve a time if after a few kilometres an athlete is running faster than expected.

The indication whether the pace followed by the athlete during a race is too fast, adequate or too slow in order to achieve a target time may for example be given with a text (such as "slow down!"), a symbol (such as an arrow), a numerical value (such as +5%), a colour (green if the pace is correct; red if it is out of the optimal range) or a value in a range.

In a preferred embodiment, the indication whether the pace followed by the athlete during a race is too fast, adequate or too slow in order to achieve a target time is indicated as a range of recommended pace on a scale, for example a range of recommended pace on a slider. The indication may include the current pace as a single value (for example 15.2 km/h) and a range of recommended pace (for example 16.5 to 18.6 km/h).

Although many runners measure their pace in number of minutes for each kilometre (or mile), and their speed in kilometre per hour (or mile per hour), both are used interchangeably in this text. Therefore, an indication of pace could be given either in kilometre per hour, in minutes per kilometre, or in any other equivalent unit.

The retrieved race profile might be an optimal race profile for the athlete. This profile indicates the optimal pace at which the athlete should run or cycle each section of his race, in order to achieve a desirable or best time at the end of the race.

The optimal race profile might be a race profile where each section is run or cycled at a constant speed, since this is the most energy-efficient way of running or cycling. However, many athletes are capable and willing of running or cycling the last section at higher speed. In addition, it is sometime more efficient to run or cycle the first kilometre, for example, at higher speed in order to leave the pack and avoid jams in some races. Obviously, the optimal race profile also depends on each race, for example on the altitude profile of each race. Therefore, the optimal race profile might be determined for each race, and depending on the level of the athlete, and is not necessarily a profile where each section is run or cycled at the same constant pace.

Alternatively, or in addition, the retrieved race profile might include a current race profile followed by the athlete, and based on the intermediate time and on previous races of other athletes. In this embodiment, the profile of the current race of the athlete is determined by measuring intermediate times all along the race, and classified as one of a plurality of standard race profiles determined from races of other athletes. This current race profile might be used for determining the information given to the athlete. For example, a specific pace recommendation could be given to an athlete who started a race with a "fast starter" race profile, and a different pace recommendation could be given to another athlete classified as "slow starter".

The method may further comprise:
determining the level of said athlete from previous races or trainings of said athlete, or from information given by said athlete in said wearable device;
using said level for determining said race profile.

For example, an athlete with a good level is less likely to be assigned to a race profile corresponding to "fast starters" than a less good athlete who achieves the same first intermediate times. A same time to run a first section of the race might be found adapted for an athlete with a good level, and too fast for a beginner with a less good level.

An athlete level may correspond to a range of VO2max values, or to a predicted time to run a given distance.

In one aspect, the method may further comprise:
before said race, determining from said previous race a plurality of normalized race profiles, said race profile corresponding to a normalized non-linear function of time over distance (t=f(d)), said normalized function being determined from a group of athletes running over the same distance, multiplying each intermediate time of each athlete by an athlete-dependent factor so as to normalize the end race time or all athletes, and determining a normalized function or a series of normalized intermediate times matching the normalized intermediate times of said athletes in the group;
during said race, retrieving the closest normalized race profile followed by the athlete as said race profile.

In one aspect, the method may further comprise:
during said race, measuring a plurality of physiological parameters of said athlete;
using at least some of said parameters for selecting or adapting the optimal or current race profile.

In one aspect, the method comprises steps during which:
during said race, the athlete enters an indication describing how good he feels;
using said information for selecting or adapting the current or optimal race profile.

The step of retrieving a current race profile can be defined as a categorization of the current race into one among a plurality of predefined profiles. Each input feature vector, corresponding to a plurality of running or cycling intermediate times during a race of an athlete, is assigned to a corresponding profile function, preferably considering an a priori known level of the athlete.

The classification can be performed with a linear regression method.

The classification can be performed with a support vector machine.

The classification can be performed with a neural network.

The predefined race profiles may be defined by training a neural network, or another self-learning structure.

The step of retrieving a race profile may comprise feeding a neural network or another self-learning structure with said intermediate times, and outputting said current race profile and/or said information.

The method may include a step of transmitting the actual intermediate times of the athlete to a remote machine, such as a remote server, and using those intermediate times for computing new race profiles.

At least some of the race profiles may be dependent on a particular race. For example, a first set of race profiles may be defined for the New York marathon and a second set of race profiles may be defined for the Berlin marathon. Therefore, the method thus considers the fact that various segments of different races are not run or cycled at the same pace depending on the event.

The invention is also related to a wearable device arranged for providing at least one of the following information to an athlete during a race such as a running or a cycling race:
- a race time prediction
- a probability to achieve a target time at the end of the race;
- and/or an indication whether the pace followed by the athlete is too fast, adequate or too slow in order to achieve a target time, said apparatus comprising
- an inertial sensor and/or a positional sensor for measuring a plurality of intermediate times during said race;
- a processing unit arranged for retrieving, based on said intermediate time and on previous races of other athletes, a race profile as non-linear function of time over distance (t=f(d)), and for determining said information based on said race profile.

The device may further include a memory for storing a plurality of predefined race profiles.

BRIEF DESCRIPTION OF THE DRAWINGS

The invention will be better understood with the aid of the description of an embodiment given by way of example and illustrated by the figures, in which.

DETAILED DESCRIPTION OF POSSIBLE EMBODIMENTS OF THE INVENTION

Figure 1:
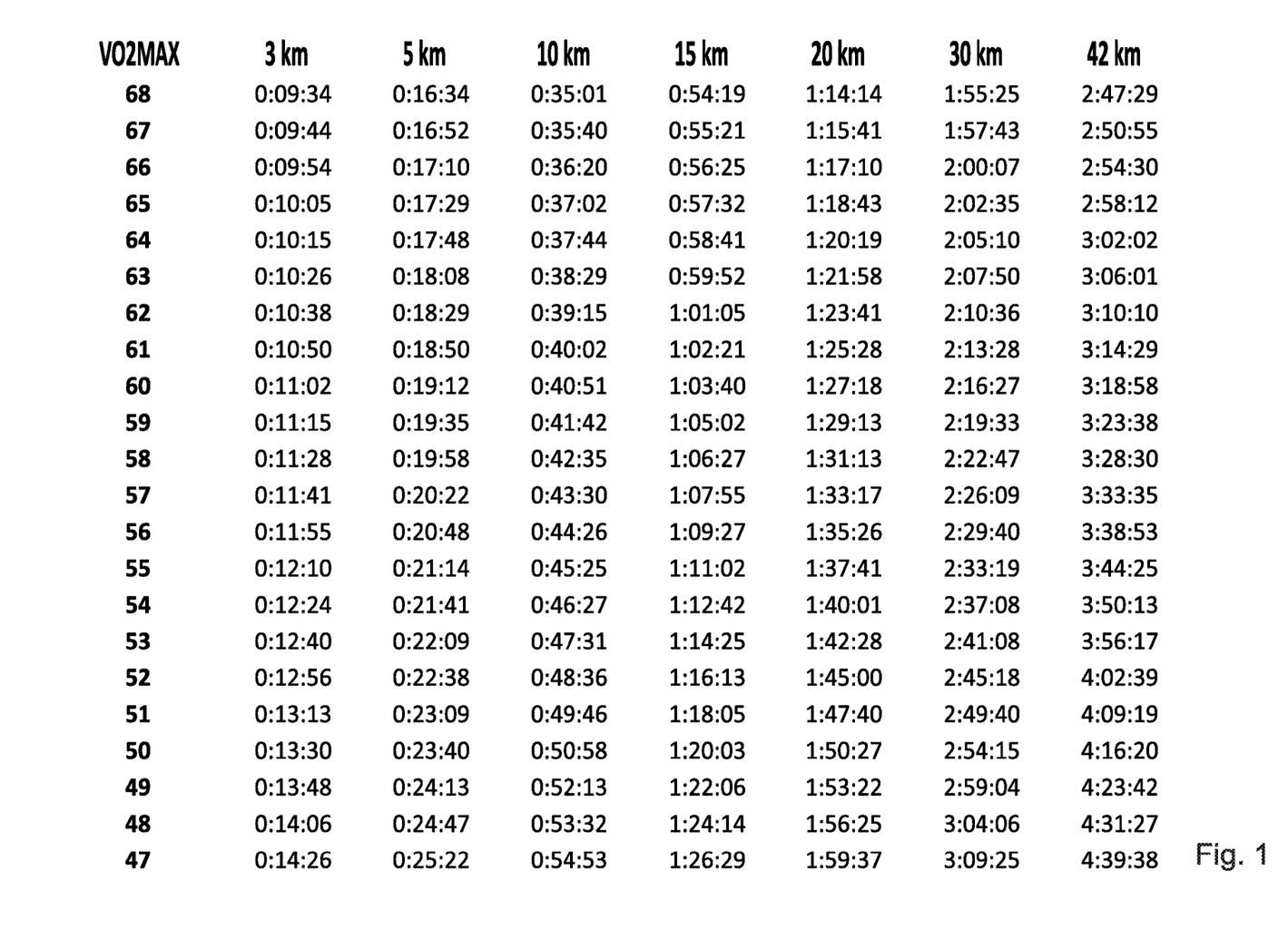
FIG. 1 is a chart showing average running times over various common distances as a function of VO2max.

FIG. 1 is a chart indicating the time needed by runners in order to run over a variety of common distances, as a function of their VO2max. Those charts are known as such and frequently used by many runners in order to determine the optimal pace. They don't consider the race profile, such as for example the deviations from the predicted time when a runner starts to fast or too slowly.

Figure 2:
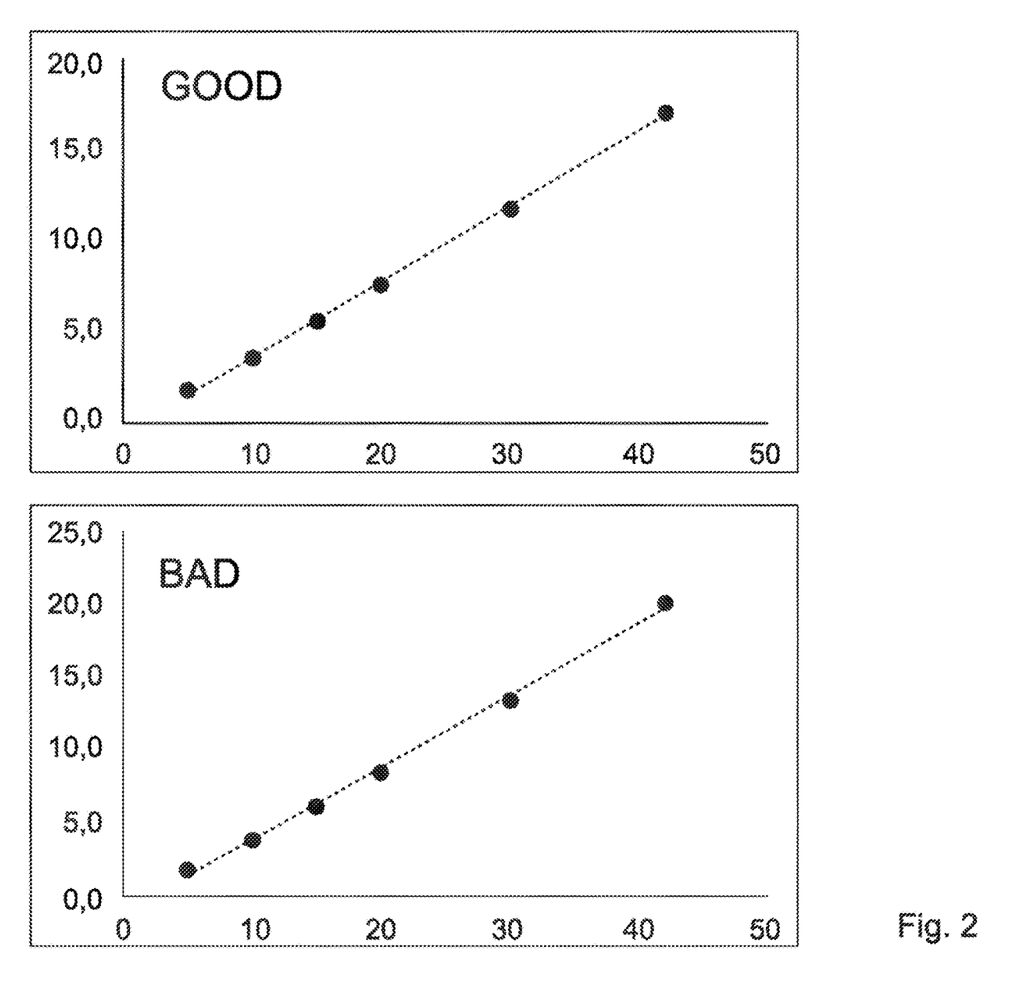
FIG. 2 shows a race profile t=f(d) for a good marathoner (top chart) and for a less good marathoner (bottom chart). The time is normalized so that all athletes finish the race in a normalized time=20.0
Figure 3:
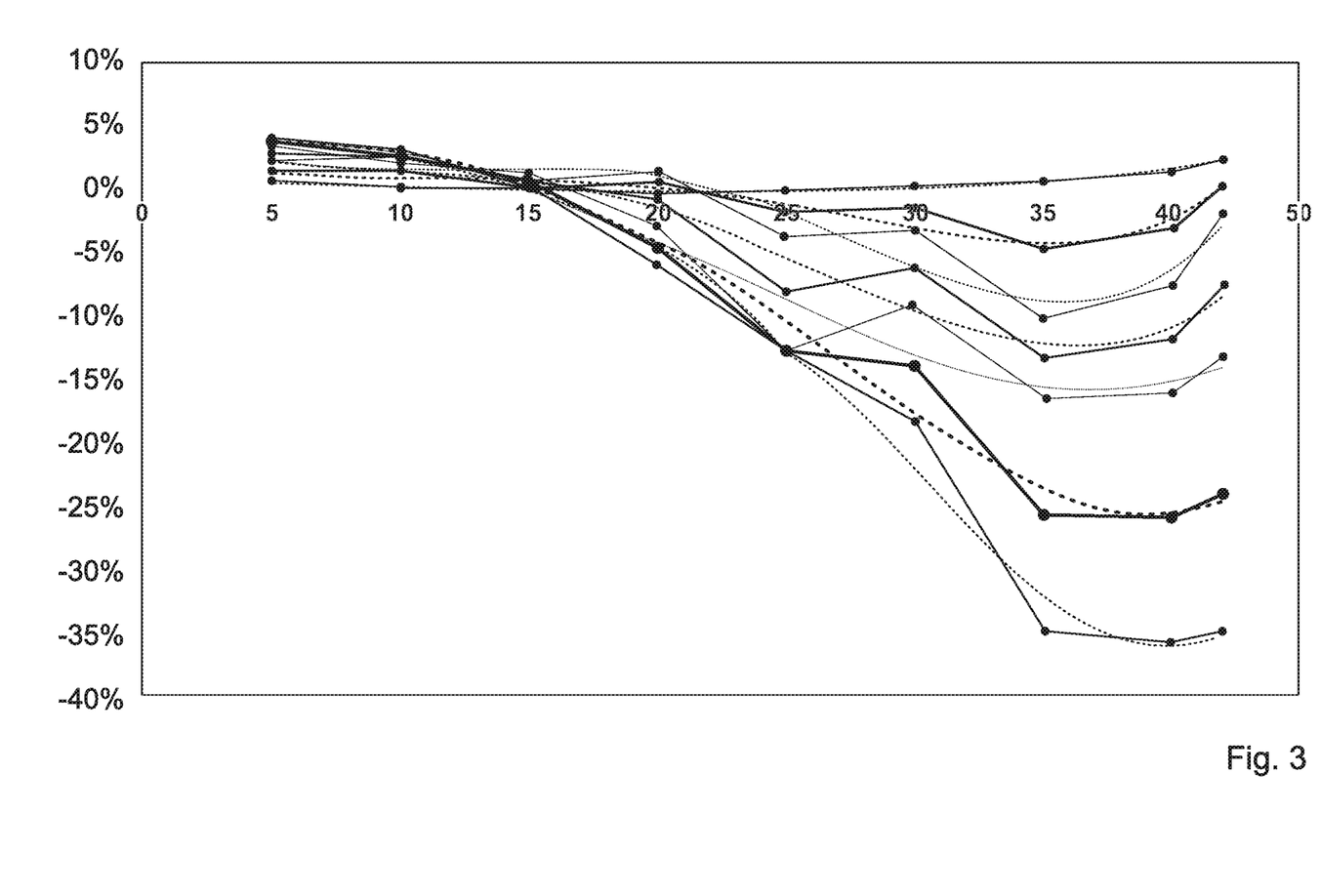
FIG. 3 shows 7 different race profiles. Each full line is made up of segments between average intermediate times measured for all athletes in each group. The dotted lines are binomial functions that best approximates each sequence of average intermediate values. The vertical axis indicates variations from the ideal race ran at constant speed, in percent.

FIG. 2 shows two charts representing race profiles of one good group or athletes (top) and of one less good group of athletes (bottom). Race profiles from a large number of athletes are collected and grouped into clusters so as to define a limited number of race profiles. The grouping may be based on the relative difference between the expected time at the end of the race (and possibly at each intermediate time) and the actual time, in percent. A clustering system, such as for example a self-learning system, for example a neural network, trained with example races of runners, may be used. Alternatively, race profiles may be manually clustered in order to define a limited number of predefined race profiles.

The race profiles may be gender dependent. The race profiles may also be race dependent. For example, a race profile may be defined for the New York marathon, and a second race profile may be defined for the New York marathon.

The times are preferably normalized before the grouping. In the example, the times are normalized as a function of the expected race time, so that the time target for each athlete is a common value, 20 in this example. Therefore, a race profile can be computed from intermediate times of athletes of different levels but having similar relative deviations at each intermediate time. For example, two athletes targeting a race time of 2 h30 and 5 hours respectively may both be assigned to a common race profile corresponding to "fast starters". Race profiles are therefore independent of the level of the athlete.

Figure 5:
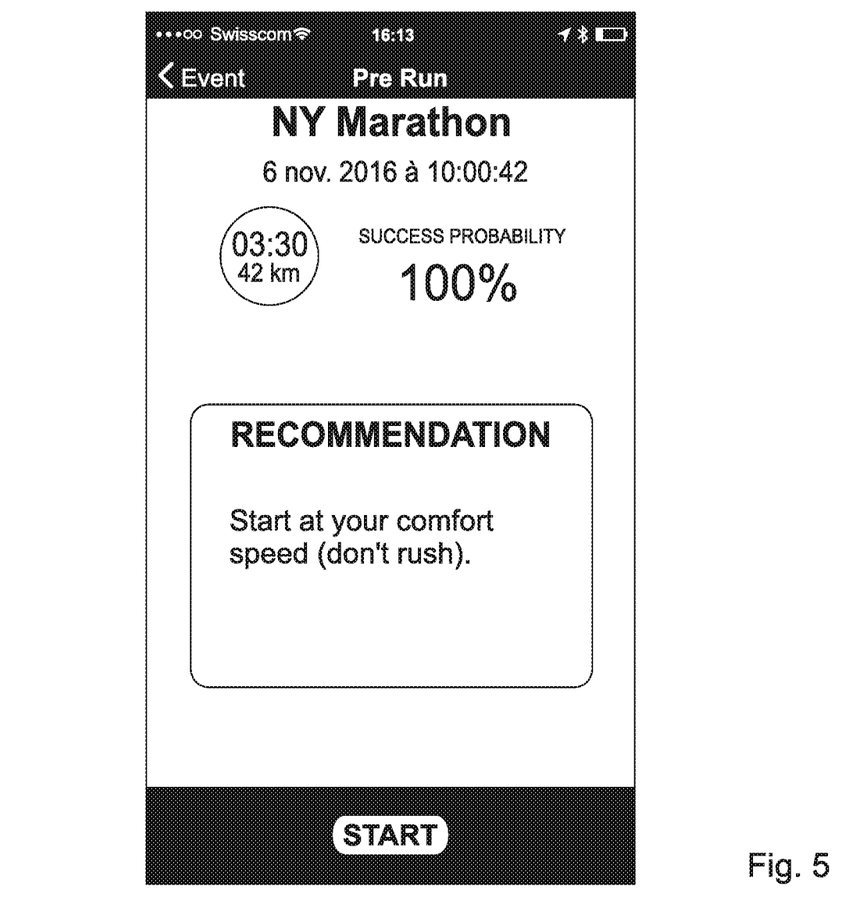
FIG. 5 is an example of information displayed on a wearable device before a race after the entry of some basic data by the athlete.

Examples of race profiles are illustrated in FIG. 5, and may be stored as an array in a wearable device used by the athlete during a competition. Alternatively, or in addition, the races profiles may be converted in equations, such as for example polynomial equations, that approximate best the values measured in each group.

During a race, the processing unit in the athlete's device determines the actual current time at a plurality of distances measured with an inertial sensor or location system, and determines from those current times a predefined, standardized race profile that best matches the measured values.

Even if the standardized race profiles are level independent, the race profile assigned to an athlete depends on his level (such as for example his VO2max value, or an expected time previously indicated by or determined for the athlete). For example, an athlete who needs a given time to run the first kilometer may be assigned a race profile "fast starter", while another athlete with a better level but running the first kilometer at the same speed might be assigned a different race profile, for example a race profile corresponding to "slow starter".

The assignment of race profile may be changed during the race. For example, a runner might be classified as a "fast starter" after two kilometers, and as an "average runner" after ten kilometers (for example if he applied a correction).

The number of standardized race profiles may be higher at the end of the race than at the beginning.

The selected race profile may also depend on physiological measures of the athlete during the race. For example, the processing unit may detect that an athlete is exhausted after 30 kilometers and assign him a race profile grouping athletes exhausted after 30 kilometers. Alternatively, those measures are used as correction or ponderation of a previously selected race profile.

Other athlete-dependent parameters may be considered for this assignment, such as the athlete size, weight, age, gender, biomechanical and/or physiological parameters, etc.

Alternatively, or in addition, the device might also determine an optimal race profile for the athlete, in order to achieve a desired or best time. This optimal race profile might depend on the previously known level of the athlete. It might be adapted during the race, based on measured intermediate times. It might also depend on the race.

In addition, environmental parameters such as temperature, humidity, etc could be retrieved from the Internet and considered and used for determining the optimal and/or current race profile.

Those environment-dependent parameters might be used for the selection of the current race profile the athlete is following. For example, the software in the wearable device might select a race profile corresponding to "fast starters" when the temperature is hot, even if the athlete is starting at a speed that would be considered normal under other weather conditions.

Those environment-dependent parameters might also be used for the selection of the optimal race profile the athlete should follow.

Some race profiles may be dependent on individual races. For example, a set of standard race profiles might be prepared for the New York marathon, and a different set of race profiles for the Berlin marathon. An athlete needs to indicate the race he is doing and the software in his wearable device will then select, after a few kilometers, one of the race profiles corresponding to this race that the athlete seems to follow, based on his level or expected end time and on his first intermediate times. Alternatively, the race is determined automatically, based for example on indication from a GPS and/or calendar.

In an embodiment of the invention, the predicted race profiles are determined during a race with a neuronal network or another self-learning structure. In this embodiment, parameters of the athlete such as his intermediate times, and possibly his level, target time, and/or physiological parameters such as pulse rate, instantaneous power, regularity, environmental parameters, etc, are input to a neuronal network or self-learning structure trained with corresponding parameters from previous races performed by another athlete. The neuronal network or self-learning structure outputs predicted race profiles for the current athlete, or information such as predicted next intermediate and end time, probability to achieve a given target, and/or instructions for adaptations of the pace.

Figure 6:
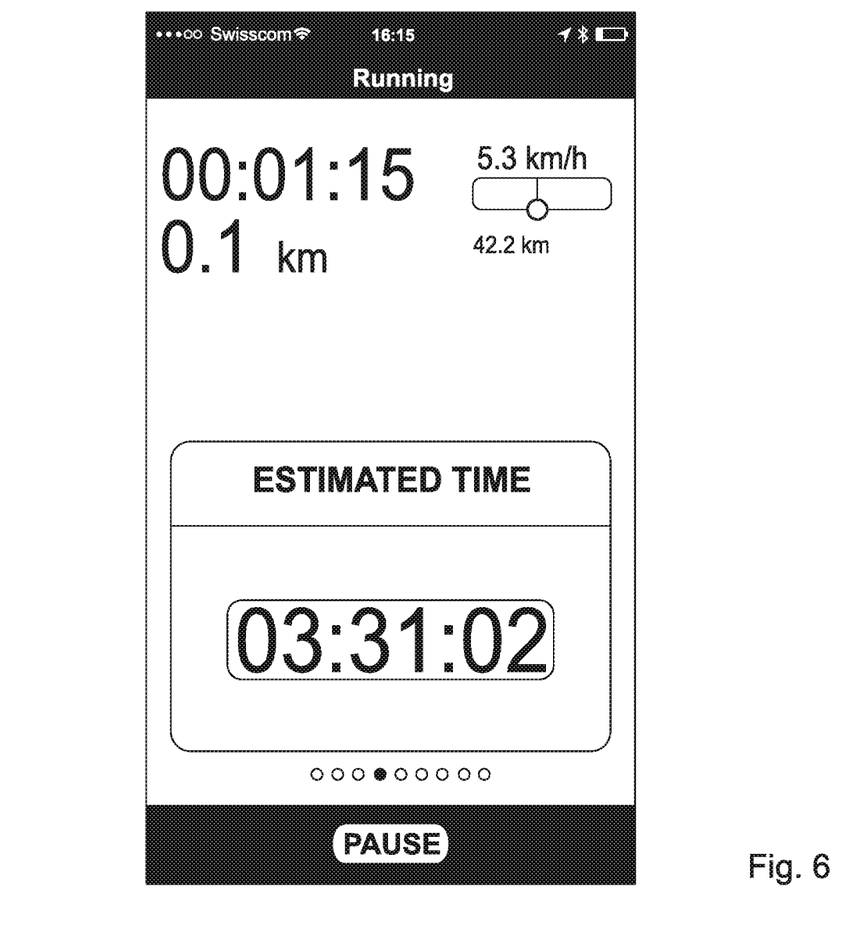
FIG. 6 is an example of information displayed on a wearable device during a race, showing the predicted time at the end of the race.

FIG. 6 illustrates an example of possible wearable device 4 according to an embodiment of the invention. In this embodiment, the wearable comprises two components: an acceleration measuring device 3, and a user interface module 5. Both components may also be integrated in one device.

Figure 11:
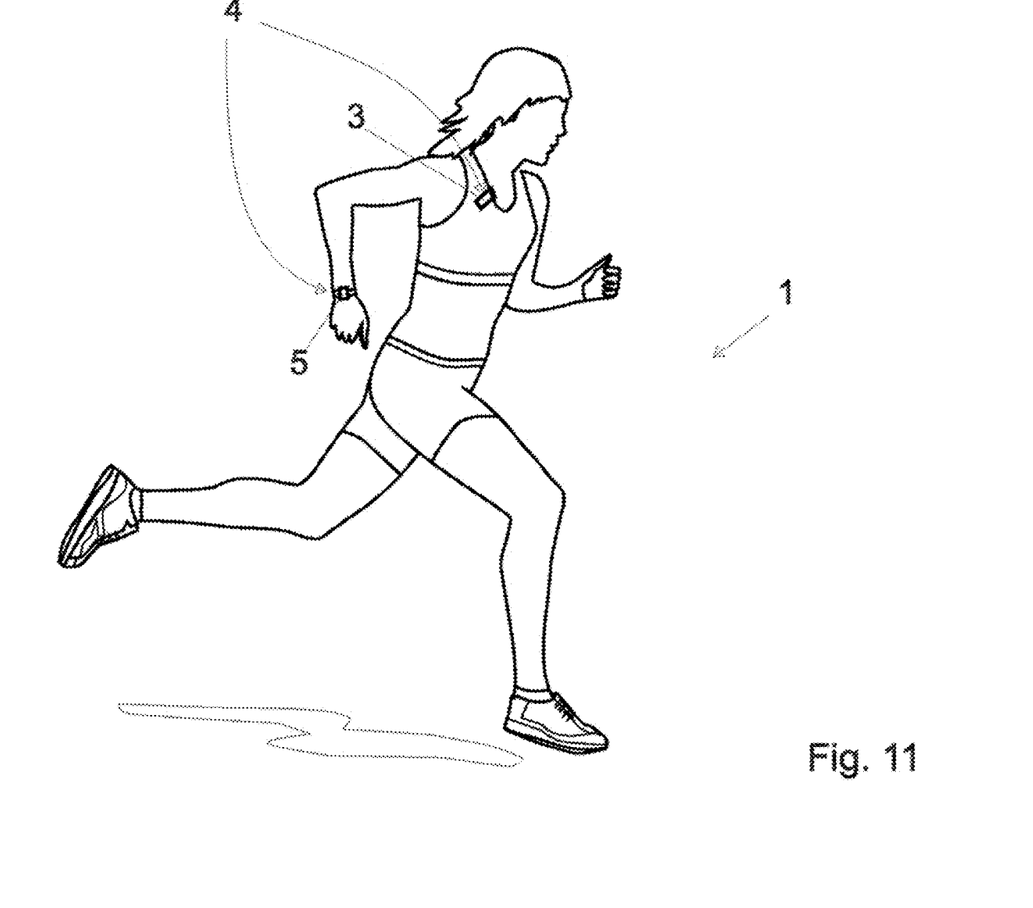
FIG. 11 illustrates an example of possible wearable device according to the invention.

The acceleration measuring device 3 is preferably intended to be worn on the athlete's body. In the embodiment of FIG. 11, it is worn close or in fixed relation to the athlete centre of mass, for example on his torso or on his head. In another embodiment, it is worn on the wrist, on a shoe, in a headset. It comprises for example a 3-axis MEMS-based accelerometer, for measuring the accelerations of the athlete along three axis and his speed along the anteroposterior axis. The device 3 may also, optionally, include a 3-axis gyroscope. The device 3 may also include a positional receiver, such as a GPS, Glonass and/or Magellan receiver, for determining the position and speed of the athlete, and thus determining when intermediate times needs to be measured.

The acceleration measuring device 3 preferably also comprises a microprocessor unit, or a microcontroller, or a FPGA module, which can read the raw data from the accelerometer and perform some processing algorithms on these data, for example in order to filter noise.

The accelerations measured with the device 3 are preferably converted into accelerations of the athlete's centre of mass along the vertical, posterioanterior and mediolateral axis; for example, the vertical direction may be roughly determined during the flight phase as the only acceleration to which the athlete is exposed, while the posterioanterior direction is the main direction of progression in the horizontal plane.

The device 3 further preferably includes a wireless interface, such as a Bluetooth, ZigBee, WiFi or ANT interface, for transmitting the processed acceleration data to a remote device such as the user interface device 5, and for receiving commands from this remote device.

The user interface device 5 may be for example a wristwatch, a smartphone, a head-up display, a headset, etc. It also includes a processor for further processing the data received from the device 3, and for determining the above described various powers. A display and/or an audio interface can be used for presenting the power information to the athlete.

Figure 4:
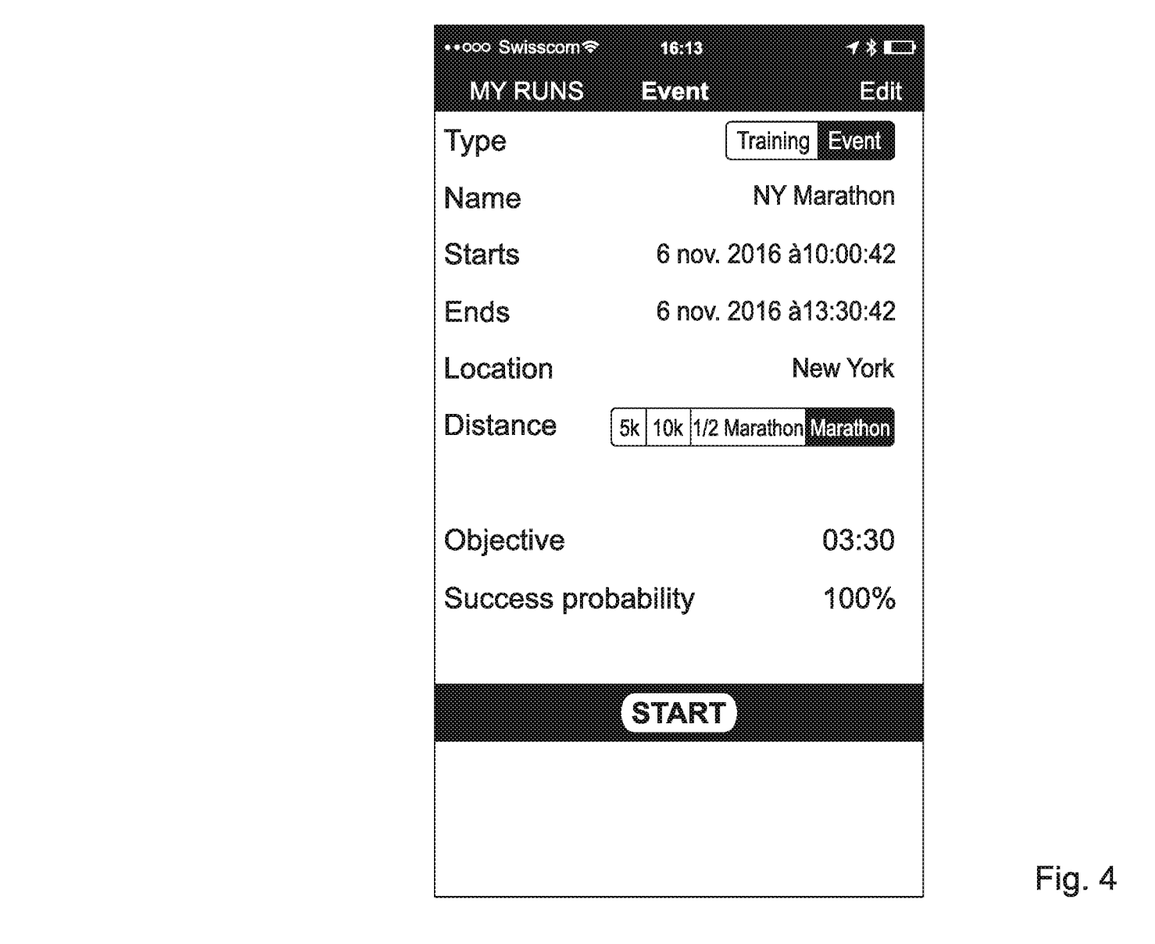
FIG. 4 is an example of information displayed on a wearable device before a race.

FIG. 4 illustrates an example of information displayed on the wearable device, for example on his wristwatch, smartphone or on a display of the acceleration measuring device. This information is displayed before the race and allows the athlete to select a distance (here a marathon), a specific race (here the New York marathon), and an objective for the race (here 3 h30). Other parameters such an athlete level, weight, age, gender etc might be entered with this screen or retrieved from an athlete profile stored in the wearable device and previously entered or otherwise determined.

This display also indicates a probability that the given target (here 3 h30) will be achieved. If this target is realistic and/or in line with the athlete level as indicated or determined with previous races (for example his VO2max), the probability will be 100%.

FIG. 5 illustrates another information displayed by the user's wearable device after the information of FIG. 4. It includes a summary of the previously entered information, as well as a recommendation. The recommendation might be generic and identical for all races, all distances and/or all runners. It might also be a recommendation specific for the user, for his target (for example "your target is ambitious, we recommend to start at a pace of 12 km/h), and/or take physiological and/or environmental conditions into account (for example "temperature will be warm. Drink enough before and during the race").

FIG. 6 illustrates an example of information displayed on the wearable device during the race. The software module has already collected a few intermediate times, as well as possibly other parameters, and determined a likely race profile the athlete is following. By extrapolating this profile, and possibly applying corrections depending on the parameters, the module estimates and indicates the predicted time at end of the race. The display might also indicate the current speed or pace of the athlete and indicate whether this speed/pace is the recommended range, too fast or too slow. The module might also indicate a probability that the previously indicated target (3 h30) can still be achieved.

Figure 7:
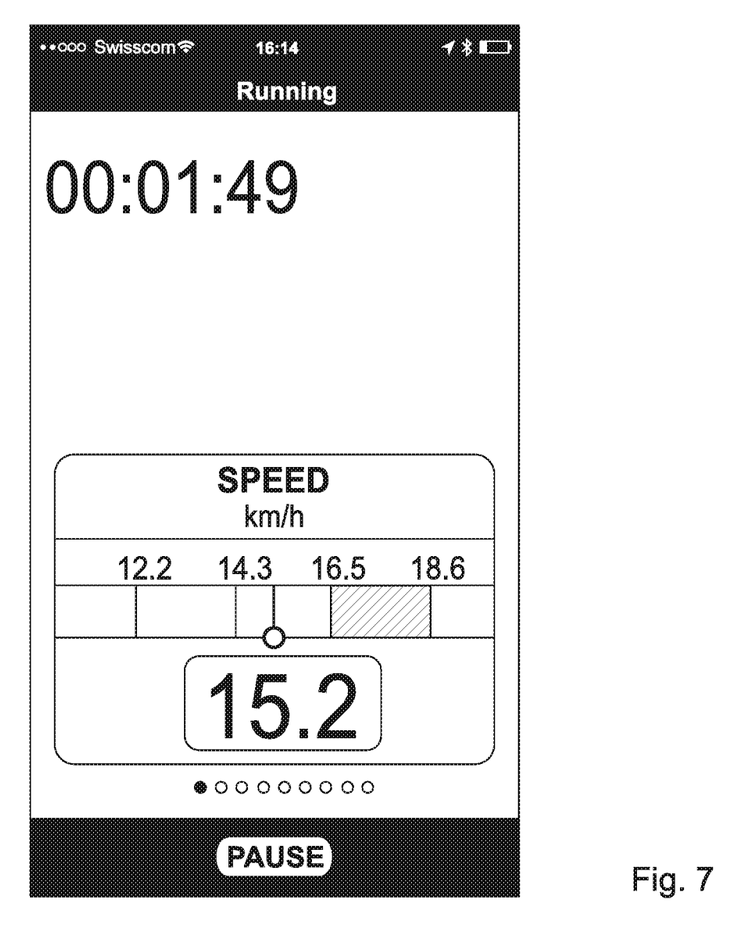
FIG. 7 is an example of information displayed on a wearable device during a race, showing the current speed and indicating whether this speed is in a recommended range.

FIG. 7 illustrates another example of information displayed on the wearable device during the race, indicating the race time and the current pace of the athlete. The display preferably also indicates whether the athlete is too fast or too slow. In a preferred embodiment, the device displays a range of recommended pace on a scale, for example a range of recommended pace on a slider. The slider may display the current pace as a single value (here 15.2 km/h) and a range of recommended pace (for example here between 16.5 and 18.6 km/h). This recommended pace range might correspond to an optimal race profile for the specific athlete's level and/or for the specific race.

Figure 8:
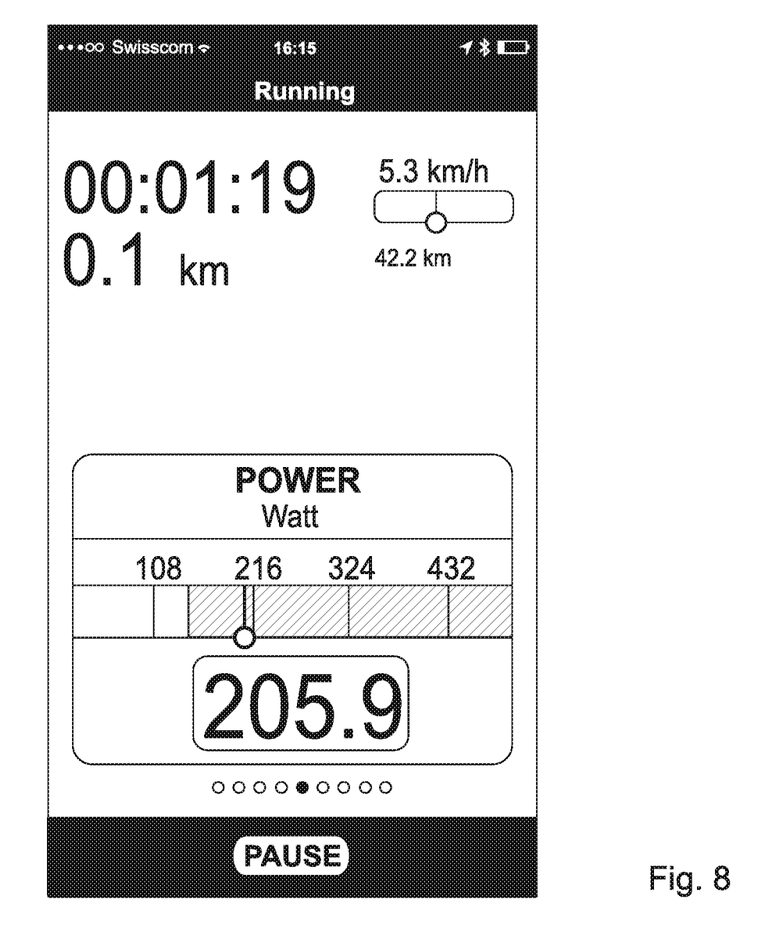
FIG. 8 is an example of information displayed on a wearable device during a race, showing the current instantaneous power developed by the athlete and indicating whether this power is in a recommended range.

FIG. 8 illustrates another example of information displayed on the wearable device during the race, indicating the current instantaneous power developed by the athlete, his time and whether the power is in a displayed recommended range in order to achieve the target. Since the instantaneous power is directly related to energy, it has been found that managing power during a race, instead of managing speed, is a more efficient way of controlling his effort in order to achieve a target or, during a training session, to obtain the best possible training result.

Figure 9:
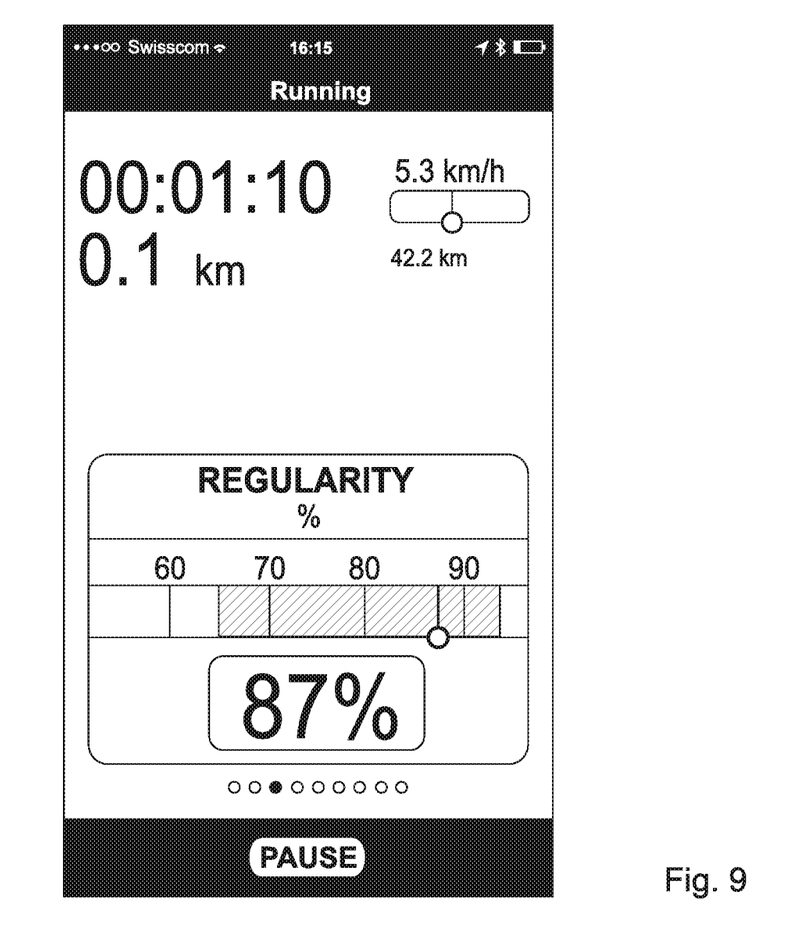
FIG. 9 is an example of information displayed on a wearable device during a race, showing the current regularity of pace and indicating whether this regularity is in a recommended range.

FIG. 9 illustrates another example of information displayed on the wearable device during the race, indicating the current regularity of the athlete, his time and whether the regularity is in a recommended range that is displayed on the diagram. Regularity might be defined as the speed regularity.

It is also possible to compute and display one, or a plurality of parameters that the athlete could adjust in order to achieve an optimal pace. For example, the display could indicate the current stride length, and/or the current cadence, which both could be adjusted in order to change the pace of the athlete.

Figure 10:
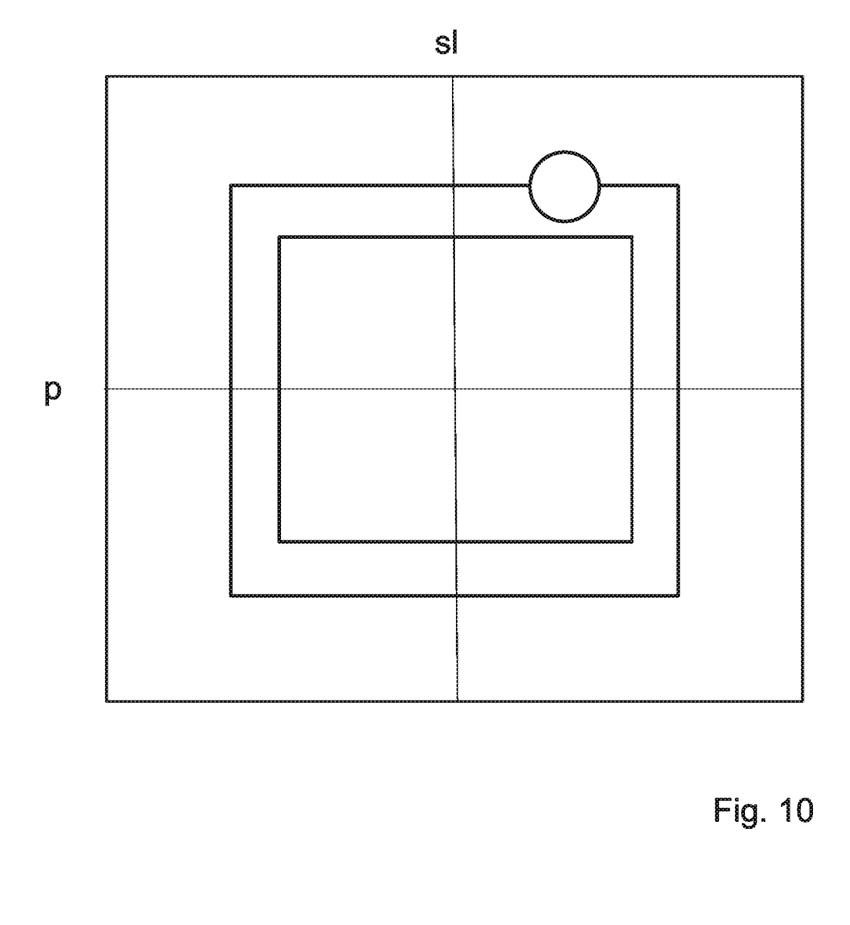
FIG. 10 is an example of information displayed on a wearable device during a race, showing two parameters (here cadence and stride length) that could be varied within two ranges in order to run at a recommended pace.

FIG. 10 shows an example of diagram showing both the current cadence (c) and stride length (sl) as well as a recommended range for those two parameters, in order to achieve a pace recommended for the athlete at the current distance of the race. This diagram could be computed and displayed on the device. Other widgets, including circular ones, could be considered.

Other parameters might be displayed during a race, with an indication whether the parameter is in the recommended range for a specific athlete and/or in order to achieve a time target.

The steps of the above described method might be executed by a processor in a wearable device of the athlete, or in a remote server. The processor might include a classifier module, for example a software classifier, in order to classify the current race profile. The classifier might use a self-learning structure, such as a neural network, which might be trained in a remote equipment.

The invention claimed is:

1. A method for monitoring performance of an athlete during a race the method comprising:
generating a plurality of race profiles by clustering data from a plurality of other athletes according to level;
determining a level of the athlete from previous races or trainings of the athlete;
receiving data from a sensor in a wearable device, wherein the data is collected by the sensor during the race;
retrieving a race profile from among the plurality of race profiles based on the level of the athlete;
applying the race profile to the data to generate a projected time for the race; and
displaying the projected time for the race on the wearable device.

2. The method of claim 1, wherein the data includes a plurality of intermediate times being measured at predetermined distances.

3. The method of claim 1, wherein the race profile is an optimal race profile for the athlete.

4. The method of claim 1, wherein the race profile is retrieved is further based on additional data collected from plurality of the other athletes.

5. The method of claim 4, wherein the race profile is determined by selecting among a plurality of standardized race profiles determined from previous races of the plurality of the other athletes, wherein the race profile is selected that best corresponds to the race profile determined.

6. The method of claim 5, wherein the selecting is based on a target time indicated by the athlete for the race and deviations from this target at a plurality of intermediate positions.

7. A non-transitory computer product storing instructions, the instructions when executed by a processor cause the processor to execute the method according to claim 1.

8. The method of claim 1, wherein the level corresponding to a VO2max of the athlete.

9. The method of claim 1, wherein the method further comprises:
displaying an indication of a recommended pace range and a current pace based on the projected time.

10. The method of claim 1, further comprising:
determining a current value of at least one race parameter based on the data;
displaying the current value of the race parameter along with a recommended range based on the projected time.

11. The method of claim 1, further comprising:
determining a current value of stride length and cadence;
displaying the current value of said stride length and of said cadence, along with a recommended range for those two parameters based on the projected time.

12. The method of claim 1, wherein the plurality of race profiles are generated from a group of the plurality of other athletes running over a same distance, multiplying each intermediate time of each athlete in the group by an athlete-dependent factor so as to normalize an end race time for the group.

13. The method of claim 1, wherein the data includes a plurality of physiological parameters of the athlete.

14. The method of claim 1, further comprising: receiving a comfort level from the athlete during the race; wherein the race profile is further retrieved based on the comfort level.

15. The method of claim 1 wherein the retrieving utilizes a neuronal network or another self-learning structure.

16. The method of claim 1, wherein the data are transmitted to a remote machine and used for computing new race profiles.

17. The method of claim 1, at least some of the plurality of race profiles are dependent on a particular race.

18. The method of claim 1, further comprising:
displaying a current speed or pace during the race, and an indication whether this speed is in a recommended range based on the projected time.

19. A wearable device for monitoring performance of an athlete during a race, the wearable device comprising:
a sensor;
a memory;
a processor that is communicatively coupled to the sensor and the memory, wherein the processor is configured to:
generate a plurality of race profiles by clustering data from a plurality of other athletes according to level
determine a level of the athlete from previous races or trainings of the athlete,
receive data from the sensor, wherein the data is collected by the sensor during the race,
retrieve a race profile from the plurality of race profiles based on the level of the athlete,
apply the race profile to the data to generate a projected time for the race; and
display the projected time for the race on the wearable device.

20. The wearable device of claim 19, wherein the memory stores the plurality of the race profiles.

21. The wearable device of claim 20, wherein each of the plurality of race profiles is normalized.

22. The wearable device of claim 19, wherein the processor is further configured to:
display an indication of a recommended pace range and a current pace based on the projected time.

* * * * *